US007955563B2

(12) United States Patent
Klepp et al.

(10) Patent No.: US 7,955,563 B2
(45) Date of Patent: Jun. 7, 2011

(54) METHODS FOR APPLYING REACTIVE FILMS CONTAINING SOLIDS TO MICROPOROUS MEMBRANES AND MEMBRANES PRODUCED THEREFROM

(75) Inventors: Juergen Klepp, Graben-Neudorf (DE); Thomas Fischer, Rauenberg (DE); Rolf Lerch, Ilvesheim (DE); Dieter Mangold, Maxdorf (DE); Juergen Schaeffler, Weinheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 27 days.

(21) Appl. No.: 11/758,804

(22) Filed: Jun. 6, 2007

(65) Prior Publication Data
US 2007/0274861 A1 Nov. 29, 2007

Related U.S. Application Data

(63) Continuation of application No. PCT/EP2005/012959, filed on Dec. 3, 2005.

(30) Foreign Application Priority Data

Dec. 7, 2004 (DE) .......................... 10 2004 058 794

(51) Int. Cl.
*G01N 27/00* (2006.01)
(52) U.S. Cl. ........ 422/101; 422/100; 422/102; 436/180; 156/230; 156/77
(58) Field of Classification Search .......... 422/100–102; 436/180; 156/77, 230
See application file for complete search history.

(56) References Cited

U.S. PATENT DOCUMENTS

| | | | |
|---|---|---|---|
| 3,630,957 A | 12/1971 | Rey et al. | |
| 3,635,808 A * | 1/1972 | Elevitch | 204/620 |
| 4,312,834 A | 1/1982 | Vogel et al. | |
| 4,780,411 A * | 10/1988 | Piejko et al. | 422/56 |
| 4,816,224 A | 3/1989 | Vogel et al. | |
| 4,824,639 A | 4/1989 | Hildenbrand et al. | |
| 5,066,398 A | 11/1991 | Soria et al. | |
| 5,158,636 A * | 10/1992 | Groitzsch et al. | 156/230 |
| 5,169,787 A | 12/1992 | Knappe et al. | |
| 5,213,689 A | 5/1993 | Kafchinski et al. | |
| 5,536,470 A | 7/1996 | Frey et al. | |
| 5,709,837 A * | 1/1998 | Mori et al. | 422/56 |
| 6,036,919 A | 3/2000 | Thym et al. | |
| 6,136,412 A * | 10/2000 | Spiewak et al. | 428/143 |
| 6,506,575 B1 | 1/2003 | Knappe et al. | |
| 2002/0068364 A1* | 6/2002 | Arai et al. | 436/113 |
| 2003/0175153 A1* | 9/2003 | Anaokar et al. | 422/56 |
| 2005/0008537 A1* | 1/2005 | Mosoiu et al. | 422/56 |
| 2005/0084982 A1 | 4/2005 | Brauner | |

FOREIGN PATENT DOCUMENTS

| | | |
|---|---|---|
| DE | 4025768 A1 | 2/1992 |
| EP | 0 016 387 A1 | 10/1980 |
| EP | 0654659 A1 | 5/1995 |

* cited by examiner

*Primary Examiner* — Jyoti Nagpaul
(74) *Attorney, Agent, or Firm* — McDonnell Boehnen Hulbert & Berghoff LLP

(57) ABSTRACT

A method for applying reactive films containing solids to microporous membranes is provided wherein the membrane is firstly moistened and the reactive film containing solids is applied to the membrane while it is still moist. Membranes produced in this manner can contain reactive films having a high proportion of film openers and can be used advantageously in diagnostic elements for detecting constituents and, in particular, large hydrophobic analytes in body fluid.

10 Claims, 1 Drawing Sheet

METHODS FOR APPLYING REACTIVE FILMS CONTAINING SOLIDS TO MICROPOROUS MEMBRANES AND MEMBRANES PRODUCED THEREFROM

BACKGROUND OF THE INVENTION

The invention concerns a method for applying reactive films containing solids to microporous membranes, membranes produced accordingly and diagnostic elements which contain them.

So-called carrier-bound tests are often used for the qualitative or quantitative analytical determination of constituents of fluids, in particular of body fluids such as blood. In these tests reagents and in particular specific detection reagents and auxiliary reagents are embedded or immobilized in appropriate layers of a solid carrier. These layers are referred to as detection elements. The liquid sample is brought into contact with these detection elements in order to determine the corresponding analyte. The reaction of liquid sample and the reagents that are present initially in a dry form and are redissolved by the sample usually results in a signal that can be detected optically or electrochemically when a target analyte is present and in particular a color change which can be analyzed visually or with the aid of an instrument usually by means of reflection photometry. Other detection methods are for example based on electrochemical methods and detect changes in charge, potential or current.

Since, in contrast to conventional laboratory tests, the detection reagents are initially present in a dry form, carrier-bound tests are often also referred to as "dry chemistry tests".

Test elements or test carriers for dry chemistry tests are often in the form of test strips which essentially consist of an elongate support layer made of plastic material and detection elements mounted thereon as test fields. However, test carriers are also known which are designed as square or rectangular wafers.

The photometric detection of low molecular analytes inn blood by means of dry chemistry test strips usually comprises the separation of erythrocytes which interfere with the photometric measurement.

The enzymes required for the analyte detection are usually located in a water-resistant, insoluble film in which a hydrophobic matrix consisting of film formers contains all or at least some of the detection reagents (i.e., essentially enzymes and indicator system), into which the sample penetrates and in which the color-forming reaction takes place. These films are applied by means of various established coating methods (e.g., knife-coating) on non-absorbent, mechanically stable support materials (such as, e.g., Pokalon® foil made of bisphenol-A polycarbonate).

The term film former means polymers which allow mechanically stable, water-resistant reagent layers to be coated (e.g., Propiofan® a vinyl propionate plastic dispersion).

In addition, these reactive films usually contain swelling agents. Swelling agents are water-soluble polymers which substantially influence the viscosity of the coating paste, which result in a fine dispersion of the reagents in the hydrophobic partial zones of the water-resistant layer and which facilitate the penetration of the sample into the layer (examples are alginate, Keltrol®, Gantrez®, Eudragit, etc.)

The "open porosity" and thus the ability of the analyte to penetrate into the reactive film can be positively affected by the addition of fillers (also known as film openers) (cf., e.g., U.S. Pat. No. 4,312,834). Fillers are water-insoluble, non-swelling, readily wettable, fine, inorganic or organic particles which do not optically scatter light or only to a slight degree and enable even relatively large molecules (for example lipids in the form of lipoproteins) and even cells (e.g., erythrocytes) to penetrate into water-resistant films. Examples of fillers are chalk, cellulose, diatomaceous earth, Celatom, kieselguhr, silicic acid, etc.

In the first generation of blood glucose test strips (e.g., "Hämoglukotest" 20-800 from Boehringer Mannheim, cf., also U.S. Pat. No. 3,630,957) the reactive film only contained a film former (Propiofan®) and a swelling agent (alginate) in addition to the detection chemistry. In the case of these very dense i.e., less open-pored, wipe-resistant films erythrocytes cannot penetrate into the reactive film, although tow molecular weight constituents of the blood such as in particular glucose are indeed able to penetrate. Hence, a separate blood separation was not necessary. The drop of blood in which it was intended to determine blood glucose was simply applied directly onto the reactive film of the test strip. After one minute incubation of the blood drop on the reactive film, the blood was wiped off, after a further minute reaction time the color development could be read from the same side of the strip to which the blood was previously applied as a measure of the analyte concentration.

Hence, it was for the first time possible to detect glucose directly in whole blood. Since these reactive films contained no fillers, they only allow the slow penetration of low molecular weight, readily water-soluble analytes such as glucose but not the detection of large and hydrophobic molecules (such as, e.g., cholesterol (CHOL), HDL (high density lipoprotein, i.e., lipoproteins of higher density), triglycerides (TG), creatine kinase (CK), etc.).

The use of qlass fiber fleeces to separate erythrocytes (see among others U.S. Pat. No. 4,816,224) especially in combination with open-pored reactive films containing fillers (e.g., the test strips of the Reflotron product line from Roche Diagnostics and later the so-called "non-wipe tests" of the Accutrend line from Roche Diagnostics) was a milestone in the development of dry chemistry tests for detecting analytes in whole blood. In addition to considerably more rapid kinetics, especially with regard to the penetration of the analyte into the detection film, enzymatic reaction and color reaction, these test superstructures also enable the detection of relatively large, hydrophobic molecules (e.g., CHOL, HDL, TG, etc.).

However, a disadvantage of the glass fiber fleece technology is the relatively unfavorable ratio of the volume of usable plasma to the blood volume used (also referred to as blood/plasma yield in the following). Furthermore, the supply of oxygen to the reactive film proved to be a limitation in the case of an oxidative analyte detection (i.e., in an analyte detection using analyte oxidase and reaction of the hydrogen peroxide reformed with peroxidase in the presence of an indicator which is converted in this process from a (usually colorless) reduced form into an (usually colored) oxidized form) especially in so-called stacked structures (glass fiber fleece for separating the erythrocytes and the reactive film from a stacked composite; the blood sample is applied to the glass fiber fleece, it penetrates the glass fiber fleece while separating the red blood cells and the serum or plasma formed in this manner penetrates into the underlying reactive film layer where the actual detection and indicator reaction takes place which can then be observed from the side of the stacked composite that is opposite to the blood application site) so that it is only possible to achieve a measuring range that is limited at the top end.

Thus, in order to reduce the blood volume, the most recent generation of test strips uses blood-separating membranes (cf., e.g., European Patent No. A 0 654 659) or very thin one-layer or two-layer films (cf., U.S. Pat. Nos. 5,536,470 and 6,036,919). The blood/plasma yield of such membrane-based systems is usually considerably more advantageous than is the case with glass fiber technology. Both membrane-based systems are elucidated in the following.

U.S. Pat. No. 5,536,470 discloses test fields which consist of a thin film layer. A sample of whole blood is applied to one side of the film layer. A color reaction can be detected from the opposite side without the erythrocytes being able to penetrate from the sample application side to the detection side. The film layer can be coated on a transparent support (e.g., foil) or on a membrane. Hence, the film disclosed in U.S. Pat. No. 5,536,470 acts as a combined blood (colored substance) separation and detection layer. A high proportion of pigment is necessary to fulfill the former function (blood (colored substance) separation), i.e., the pigment content is at least 30% by weight in this case based on the solids content of the film-forming paste. A high content of film former is also necessary to ensure the mechanical stability of such film layers containing a high proportion of pigment. The pigment and film former should be present in approximately the same weight ratio. Inert fillers (i.e., so-called film openers) should if possible not be present in these film layers or, if they are present, then they should only be present in the film forming paste in very small amounts (less than 10% of the total solids content) because otherwise the blood-separating property of the film layer is no longer ensured. However, due to the low filler content in the film-forming paste of at most 10%, the films disclosed in U.S. Pat. No. 5,536,470 are not sufficiently open-pored to be permeable to large, hydrophobic analytes (e.g., lipids).

In the case of a glucose detection using thin two-layer films on transparent foil, the first layer (i.e., the layer which rests directly on the foil) is a reactive film which contains film formers, swelling agents and an optically transparent filler (e.g., Transpafill®, a sodium aluminum silicate from Degussa) in addition to the enzyme-indicator system. In analogy to a wet chemical photometer test, the transparent first layer forms quasi the cuvette in which the photometric analyte detection occurs. The second layer applied to the first layer contains a high proportion of a highly refractive pigment (e.g., titanium dioxide) while dispensing with film openers or fillers. Blood is applied directly to the second layer, the photometric detection takes place from the opposite side of the test strip through the transparent support foil in the first layer.

The optically opaque, less open-pored second layer fulfills in this case a double function. On the one hand, as a blood-separating film it prevents erythrocytes from penetrating into the reactive first layer, and on the other hand, it reflects the light falling through the first layer and prevents the red erythrocyte color from shining through to the detection side.

The advantage of such a system compared to erythrocyte separation by means of a glass fiber fleece is the lower sample volume that is required and the rapid kinetics when detecting low molecular analytes.

The disadvantages of this two-layer structure is that large hydrophobic molecules (e.g., lipoproteins, cholesterol, triglycerides, HDL, etc.) cannot diffuse through the blood-separating second layer and can thus not be detected in the first layer.

Hence, an alternative is to use blood-separating membranes. Blood-separating membranes (i.e., membranes generating plasma or serum from whole blood) are very asymmetric membranes (usually polyether or polyether sulfone, e.g., BTS-SP-300 from the Pall Co., PrimeCareX or SG from Spectral Diagnostics), i.e., membranes whose pore diameter is not uniform, but rather have an open-pored and a narrow-pored side. Blood is usually applied to the more open-pored side of the membranes. The erythrocytes are held back in the tapering pores as the sample material passes through the membrane (cf., European Patent No. 0 654 659).

Blood separating membranes are basically used in two forms in dry chemistry test strips. In the so-called one layer structure the blood-separating membrane in addition to blood separation also fulfills the function of a support for the detection chemistry. For this purpose the membrane is impregnated with a system comprising an aqueous indicator and detection system (e.g., by means of bath impregnation or slot nozzle metering).

In order to ensure a rapid dissolution of the impregnated and dried enzymes and a rapid wetting of the membrane by the sample material, wetting agents are usually added to the impregnation solution.

A disadvantage of the one-layer membrane structure is that the membrane is optically non-transparent in the dry state (the refractive index of air is about 1.00; the refractive index of the membrane is about 1.35-1.38, i.e., the difference between the refractive indices is about 0.35-0.38 so that the membrane appears to be non-transparent), however, it becomes optically considerably more transparent in the wet state (the refractive index of water is about 1.33 so that the difference between the refractive indices is only about 0.02-0.05) and thus the intrinsic color of blood of the erythrocytes separated in the lower membrane zones shines through and influences the photometric measurement.

This can be reduced or prevented by adding white pigments (e.g., titanium dioxide, refractive index about 2.55) to the impregnation solution. Since optically opaque white pigments have particle sizes in the range of half the wavelength of the light to be reflected (0.2 to 0.4 µm), they can enter the pores of the membrane (which typically have a diameter of 0.2 to 10 µm) during the impregnation and thus narrow and block them and hence make it impossible or more difficult for large hydrophobic molecules to enter and pass through the membrane.

Consequently, one-layer structures with blood-separating membranes are used exclusively to detect small, readily water-soluble analytes (e.g., glucose).

A two-layer membrane structure allows many problems of the one-layer structure to be circumvented. In this case another, more narrow-pored detection membrane which absorbs the plasma from the blood-separating membrane (e.g., Biodyne A or Loprodyne=0.2/0.45 µm nylon membrane from the Pall Company) is adjacent to the blood-separating membrane. In this case optically opaque white pigments are not necessary. Furthermore, the detection system present in the second membrane does not come into direct contact with the blood-separating system which, especially in the field of lipid tests, enables the use of wetting agents that readily dissolve lipids and also have a hemolytic effect.

However, disadvantages a the two-layer structure are a complicated, expensive test configuration. The manufacturing process makes high demands on the mechanical test strip assembly because a close contact without gaps if possible has to be ensured so that serum or plasma can pass from the blood-separating membrane into the detection membrane. Inherent disadvantages of the system are the slow wetting of the test structure, an unfavorable blood/plasma yield compared to the one-layer structure and slower kinetics due to the narrower pores of the detection membrane.

Thus, in summary the disadvantages of the methods of the prior art are that open detection films having a high proportion of fillers are necessary especially to detect large hydrophobic molecules, but such open detection films alone do not ensure a separation of interfering blood components (above all erythrocytes, hemoglobin) for test strips that are analyzed optically. In contrast, suitable blood separation systems (films, membranes) allow the penetration of large hydrophobic molecules, if at all, then only to an inadequate extent. Systems that are basically suitable for detecting large hydrophobic molecules (such as the combination of glass fiber fleece and an open detection film or two-layer membrane structures) only inadequately solve the problem because they are complicated to manufacture and prone to interference and are suboptimal in their test performance (large volumes of blood required, limited upper measuring range or slow reaction kinetics).

SUMMARY OF THE INVENTION

It is against the above background that the present invention provides certain unobvious advantages and advancements over the prior art. In particular, the inventors have recognized a need for improvements in methods for applying reactive films containing solids to microporous membranes, membranes produced therefrom, and diagnostic elements containing same.

Although the present invention is not limited to specific advantages or functionality, it is noted that the present invention provides a dry chemistry test device (and a corresponding production process therefor) which enables the detection of large hydrophobic molecules and, in particular, lipids, which are present in biological samples as lipoprotein complexes, in very small amounts of whole blood, wherein a separation of red blood cells is integrated into the device and rapid kinetics of the detection reaction is achieved.

In accordance with one embodiment of the present invention, a method for applying reactive films containing solids to microporous, absorbent, blood-separating membranes is provided comprising providing a microporous membrane; moistening the microporous membrane with water or an aqueous solution; and applying a reactive film containing solids to the microporous membrane which membrane is still moist.

In accordance with another embodiment of the present invention, a microporous, absorbent, blood-separating membrane is provided, which membrane is formed by the method described herein.

In accordance with yet another embodiment of the present invention, a diagnostic element for detecting constituents of body fluids is provided containing a membrane coated with a reactive film as described herein.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which.

Figure 1:
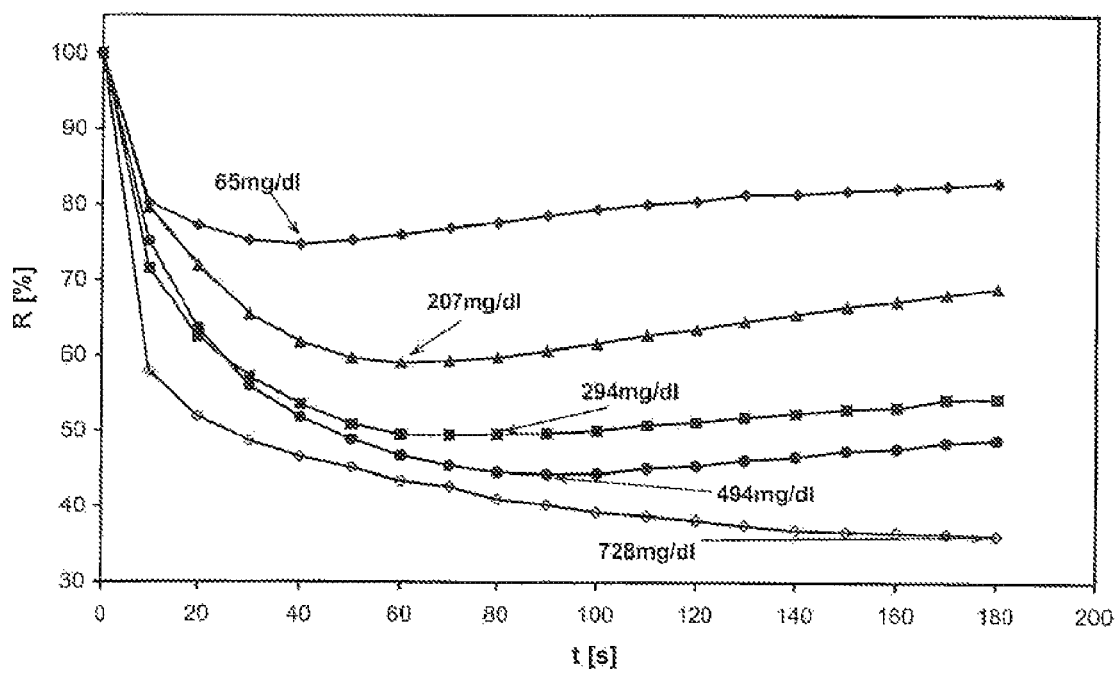
FIG. 1 shows the kinetic measurement time course for test strips which contain a "moist-coated" membrane in the presence of blood samples containing different triglyceride contents (65, 207, 294, 494 and 728 mg/dl) in which the relative reflectance (R in %) is plotted versus time (t in s)

The numerals and abbreviations in the figures have the following meaning:
  1 measurement curve for moist-coated membrane
  2 measurement curve for dry-coated membrane
  R relative reflectance
  t time
  c concentration

DETAILED DESCRIPTION OF THE INVENTION

Reactive films containing solids can be water-resistant, water-insoluble films which contain all or at least some of the detection reagents in a hydrophobic matrix of film formers. In addition to the actual detection chemistry which typically comprises enzymes, co-enzymes, mediators, indicators or indicator systems, etc., reactive films can contain water-resistant film formers, film openers and optionally optically blocking pigments (the latter being used to reduce the optical transparency) and other components known to a person skilled in the art (wetting agents, swelling agents, etc.).

According to an embodiment of the present invention, inorganic or organic and, in particular, particulate materials come into consideration as film openers (also referred to as fillers). Such film openers are known to a person skilled in the art. For example, as already mentioned above, water-insoluble, non-swelling, readily-wettable, fine inorganic or organic particles which do not scatter light or only to a slight degree and enable even relatively large molecules (for example, lipids in the form of lipoproteins) and even cells (e.g., erythrocytes) to rapidly penetrate into water-resistant films are suitable. Examples of fillers are chalk, cellulose, diatomaceous earth, Celatom, kieselguhr, silicic acid, etc. Celatom and kieselguhr have proven to be particularly suitable for the purposes of the invention.

According to an embodiment of the invention, especially organic polymers which enable the formation of mechanically stable, water-resistant reagent layers come into consideration as film formers. Such film formers are known to a person skilled in the art. For example, as already mentioned above, vinyl propionate plastic dispersions, e.g., Propiofan®, Eudragit® (a dispersion of an acrylic resin), Mowiol® (a polyvinyl alcohol), etc., are suitable.

According to an embodiment of the invention the reactive film is coated onto a microporous support layer which can also be referred to as a microporous membrane. Especially when using whole blood as a sample material, it is advantageous when the membrane has blood-separating properties, i.e., is able to retain colored components (above all erythrocytes, hemoglobin) from a whole blood sample and thus to generate plasma or serum from whole blood. Such membranes are known to a person skilled in the art. Examples are polyether or polyether sulfone membranes which are typically asymmetric. Examples of these are BTS SP 300 (Pall), Prime Care X or SG (Spectral Diagnostics).

According to an embodiment of the invention, it can be advantageous to moisten the microporous membrane before coating it with the coating paste that is intended to form the reactive film and to carry out the coating while it is still in a moist state. It can be especially advantageous to apply the reactive film coating directly after the moistening, i.e., if possible in one process step.

If reactive films are applied to membranes that have not been pre-moistened, i.e., to dry membranes, blood-separating membranes coated with reactive films are obtained which, as expected, hold back erythrocytes. The reactive film applied to the membrane fills up with plasma. In principle a color development that depends on the amount of analyte can be observed. However, dry membranes coated with reactive films exhibit only suboptimal results when analyzing blood samples especially if the analyte is a large or hydrophobic molecule (CHOL, TG, HDL, etc.). In this case the extent of color development in the reactive film is considerably less than expected.

Application of plasma containing lipids directly to this reactive film, i.e., without prior separation of blood from whole blood by means of the membrane, leads, however, to the expected color development. If the same samples are firstly guided through the dry coated blood-separating membrane, there is almost no color development despite the ensured wetting of the reactive film with plasma. This experimental finding leads to the supposition that the permeability of the membrane to large hydrophobic molecules is greatly reduced by applying the relatively open film containing fillers.

Using the triglyceride test as an example it was possible to explicitly show that the permeability of small, readily soluble, temporarily formed analyte intermediates (e.g., glycerol, $H_2O_2$) through the membrane-reactive film composite was ensured (i.e., there was no difference in color between sample application from above (directly on the reactive film) and from below (sample is applied to the membrane and penetrates this membrane before contacting the reactive film) even if the membrane was dry coated.

Furthermore, it was observed that the metastable coating pastes startled to segregate during the application of open films containing fillers and pigments to absorbent, non-premoistened membranes. The pigment and filler fractions of the coating pastes concentrated during the coating process at the doctor blade gap. This resulted in very inhomogeneous coatings.

Although it was possible to apply more stable coating pastes and thus more homogeneous films to absorbent, non-premoistened membranes by reducing the proportion of pigment/filler in the coating paste, the permeability to analytes was not promoted by this means because films with a low proportion of fillers are rather less open-pored and thus more impermeable to analytes and especially to large or hydrophobic analytes.

In accordance with an embodiment of the present invention, it is possible to apply metastable reactive films containing solids to absorbent membranes without reducing the analyte permeability if the membranes are coated in a moistened state.

This can advantageously be carried out technically by, for example, firstly guiding the membrane through a water bath in a process step and subsequently applying the paste containing solids to the membrane while it is still moist by means of a doctor blade or slot die.

A positive side-effect apart from the increased analyte permeability, is that considerably more homogeneous films are applied because the tendency of metastable pastes containing solids to segregate during the coating process is considerably reduced when using moist membranes. More homogeneous films ultimately mean improved precisions in photometric measurements and thus lower coefficients of variation in the concentration determination.

Furthermore, this process can be used to apply open-pored films on membranes by using higher proportions of filler in the coating paste.

Since this method apparently reduces the penetration of components of the reactive film into membranes during the coating process, it enables, due to the better spatial separation of blood separation (in the membrane) and reactive film (on the membrane), the reactive film components which promote the detection reaction as a whole (e.g., special wetting agents, which readily dissolve lipoproteins and activate lipases and esterases) to be added to the reactive film in a one-layer structure without at the same time causing hemolysis due to vetting agents in the blood-separating membranes.

The moistening of the membrane is typically carried out by bath impregnation, slotted nozzle impregnation or spraying. Water or aqueous solutions can be used to moisten the membrane which can for example contain buffers, wetting agents (generally also referred to as surfactants or detergents) to improve the wetting of the membrane, etc.

The method according to the invention is especially suitable for coating reactive films in which the ratio of the masses of film opener to film former is about 10:1 to about 1:1. Especially films having a ratio of masses of film opener to film former of about 5:1 to about 2:1 have proven to be particularity suitable. Reactive films having such a mass ratio are characterized by a relatively large open porosity which facilitates or allows for the first time penetration of large hydrophobic molecules into the reactive film. It was previously not possible to produce such membranes coated with homogeneous, open-pored films. Therefore correspondingly coated microporous membranes are also a subject matter of the present invention.

The reactive film is applied by means of known methods such as e.g., doctor knife coating, roller application or slot die coating.

In addition to the coated membranes according to the invention, another subject matter of the present invention is a diagnostic element for detecting constituents of body fluids comprising a membrane coated with a reactive film. Body fluids in this connection are in particular blood, serum, plasma, urine, saliva, sweat, etc., blood being typical. The constituents to be detected are typically analytes that are to be detected in body fluids and in particular large and/or hydrophobic molecules such as CHOL, TG, HDL, etc., which are present in blood in the form of lipoprotein complexes, but they also include fructosamine, creatine kinase (CK), glutamate oxalate transferase (GOT), glutamate pyruvate transaminase (GPT), amylase, hemoglobin, albumin.

An advantage of the subject matter of the invention is that the method according to an embodiment of the invention enables for the first time reactive films with a high content of fillers (based on the amount of film former) to be coated on membranes and thus to generate stable, homogeneous open films. These films are particularly advantageous for the detection of large hydrophobic analytes in whole blood. The membrane fulfills the function of blood separation, i.e., it holds back erythrocytes and optionally hemoglobin so that the blood color does not interfere with the subsequent analyte detection by means of optical methods. The intimate contact between the membrane and detection film is ensured so that a rapid and substantially complete transfer of the serum/plasma into the reactive film occurs. The analytes can be detected in a few μl of whole blood. The coating method is excellently suitable for automated processes, in particular for the large-area manufacture of reactive films coated on membranes and also in roll or tape processes.

In order that the invention may be more readily understood, reference is made to the following examples, which are intended to illustrate the invention, but not limit the scope thereof.

Example 1

Method for Applying a Reactive Film to a Blood-Separating Membrane and a Corresponding Test Device for Detecting Triglycerides in Whole Blood 1. Production of the coating paste a.) Gantrez solution:

35.5 g water is added to 58.5 g of an 85 millimolar phosphate buffer (pH 7.5). After adding 1.7 g $MgSO_4$, 5.2 g Gantrez S 97 (copolymer of methyl vinyl ether and maleic acid anhydride, GAF Corporation chemical division) is added in small portions and stirred for 3 hours until the Gantrez is completely swollen. Afterwards 4.5 g of a 32% NaOH solution is added and after a further 30 minutes stirring 0.6 g PVP (polyvinylpyrrolidone 25,000) is sprinkled in and stirred for a further 20 minutes until it has completely dissolved. Subsequently the pH of the paste preparation is adjusted with 32% NaOH to a pH of 6.7-7.0.

b.) Symperonic solution:

1.3 g Symperonic F68 (polyoxyethylene-co-oxypropylene, ICI) is dissolved in 5.3 g water while stirring for 20 minutes.

c.) 17.0 g Propiofan 70 D (50% polymer dispersion of vinyl propionate in water, demonomerized, source BASF, Ludwigshafen) is added to the Gantrez solution described in a.) and after 30 minutes stirring 26.5 g Celatom MW 25 (kieselguhr, CHEMAG) was added within 10 minutes and stirred for a further 20 minutes. Afterwards 6.6 g of the Symperonic solution described in b.) is added to the preparation and stirred for a further 10 minutes.

d.) Refloblau solution 1.7 g Refloblau (4-(4-dimethylaminophenyl)-5-methyl-2-(3,5-dimethoxy-4-hydroxyphenyl)-imidazole dihydrochloride, Roche Diagnostics) is dissolved protected from light in 23.3 g 35° C. warm water by stirring for 15 minutes on a magnetic stirrer.

e.) Titanium dioxide/Refloblau partial preparation

While protected from light 22.5 g of an 85 molar phosphate buffer (pH 7.5) is added first and 4.3 g $TiO_2$ (RN 56, Kronos Titan) is sprinkled in within 5 minutes using a dissolver stirrer at 450 rpm and afterwards it is stirred for a further 5 minutes. Finally 25 g of the Refloblau solution prepared in d.) is added within 5 minutes to the $TiO_2$ suspension and stirred for a further 30 minutes. Afterwards the $TiO_2$/Refloblau partial reparation is stored until use in a refrigerator while protected from light.

f.) ATP solution 1.7 g ATP (adenosine triphosphate; di-sodium salt) is dissolved in 3.3 g water.

g.) DONS solution 1.3 g DONS (dioctylsodium sulfosuccinate) is dissolved in 5.3 g acetone.

h.) MPSC solution 0.03 g MPSC (methylphenylsemicarbazide) is dissolved in 0.6 g 1-methoxy-2-propanol while protected from light.

i.) Enzyme solution

The following enzymes (present as lyophilisates) are dissolved successively in 15.9 g of an 85 millimolar phosphate buffer (pH 7.5) where the respective weighed-in amount of enzyme depends on the specific activity of the enzyme batch that is used.

40 kilo units (about 1.8 g) glycerokinase (EC 2.7.1.30 from *Bacillus stearothermophilus*; Roche Diagnostics, Cat. No. 0 717 398)

34 kilo units (about 2.4 g) cholesterol esterase (EC 3.1.1.13 from *Candida cylindracea*; Roche Diagnostics, Cat. No. 0 129 046)

28.9 kilo units (about 0.12 g) peroxidase (EC 1.11.1.7 from horseradish; Roche Diagnostics, Cat. No. 0 121 606)

27.8 kilo units (about 0.44 g) L-α-glycerol phosphate oxidase (EC 1.1.3.21; recombinant, Roche Diagnostics, Cat. No. 1 582 003).

j.) The following partial preparations are finally added to the Gantrez/Propiofan/Celatom preparation from c.) while stirring.

6.6 g DONS solution from g.)
5.0 g ATP solution from f.)
51.8 g $TiO_2$/Refloblau Suspension from e.)
7.0 g water for rinsing out the $TiO_2$/Refloblau solution
11.8 g Celatom MW 25
0.63 g MPSC solution from h.)
20.66 g enzyme solution from i.)
2.2 g 85 mmolar phosphate buffer to rinse out the enzyme solution.

After adding each partial solution (with the exception of Celatom) the preparation is stirred for 5 minutes. The Celatom is sprinkled in small portions within 15 minutes and the preparation is then stirred for a further 20 minutes.

The total preparation (about 250 g) is finally centrifuged for 20 minutes at 300 g for deaeration and subsequently any solids that may have been sedimented by the centrifugation are slowly resuspended by hand using a rubber wiper.

Afterwards the coating paste is passed through a 140 µm test sieve and again homogenized for 10 minutes while gently stirring.

The coating paste has the composition given in table 1.

TABLE 1

Composition of the coating paste

| | absolute | solids content |
|---|---|---|
| Gantrez S97 (as film thickener/swelling agent) | 5.2 g | 5.2 g |
| PVP (polyvinylpyrrolidone) | 0.6 g | 0.6 g |
| Propiofan dispersion (50% in water as film former) | 17 g | 8.5 g |
| Celatom (as film opener) | 38.3 g | 38.3 g |
| $TiO_2$ RN56 (as white pigment) | 4.3 g | 4.3 g |
| $MgSO_4$ | 1.7 g | 1.7 g |
| Refloblau | 1.7 g | 1.7 g |
| methylphenyl semicarbazide | 0.03 g | 0.03 g |
| ATP (di-sodium salt) | 1.7 g | 1.7 g |
| Symperonic F68 | 1.3 g | 1.3 g |
| DONS (dioctylsodium sulfosuccinate) | 1.3 g | 1.3 g |
| glycerokinase | 40 KU | 1.8 g |
| cholesterol oxidase | 34 KU | 2.4 g |
| peroxidase | 28.9 KU | 0.12 g |
| L-α-glycerol phosphate oxidase | 27.8 KU | 0.44 g |
| Acetone | 5.3 g | — |
| 1-methoxy-2-propanol | 0.6 g | — |
| NaOH (32%) | 4.5 g | 1.4 g |
| distilled water | 152.9 g | — |
| Sum | 241.2 g | 70.8 g |

The solids content of the coating past is 29%. The percentage solids content of the film former (Propiofan) based on the total solids content is 12%. The percentage solids content of the film opener (Celatom) based on the total solids content is 54%. The ratio of film opener to film former is 4.5:1.

2. Applying the Reactive Film to a Blood-Separating Membrane

A blood-separating membrane (type BTS-SP-300; article No. 955 00 12 0953 obtained from the Pall GmbH Company/63303 Dreieich) is coated with the coating paste produced as described in section 1.) by means of the method described in the following in order to generate a reactive film.

a) An approximately 1 meter long piece of membrane (BTS-SP-300) is firstly pulled through a stainless steel trough filled with water and afterwards the excess water standing on the membrane surface is removed using a rubber wiper. The coating paste from 1.) is doctor coated onto the membrane that is still moist at a feed rate of 1.5 m/min and a knife gap of 150 μm, The membrane coated in this manner (referred to in the following as "moist-coated membrane") is subsequently dried for 5 minutes at 50° C.

Finally the membrane is cut into 4.0 mm wide fine-cut rolls using a cutter spindle. The fine-cut rolls are stored dry until further use.

b) As a comparison a second piece of BTS-SP-300 is coated with the identical coating paste without previously pulling the membrane through a stainless steel trough filled with water (referred to in the following as "dry-coated membrane").

3-Production of Test Strip Functional Models to Detect TG in Whole Blood

An approximately 200 μm thick polyester foil (so-called spacer layer) coated on both sides with double-sided adhesive tape out of which 1.5 mm wide capillaries (capillary length 35 mm) running longitudinally to the subsequent test strips were previously cut at a distance of 5.0 mm with the aid of a cutting plotter (type Aristomat 1310 from the ARISTO Graphic Systems Company; 22525 Hamburg) by means of a "kiss cut" is glued onto a 5 mm wide and 78 mm long support foil (Melinex). A 5 mm×25 mm polyester net (type Petex 07-98/34 from the Sefar Company/CH-9410 Heiden) having a mesh width of 250 μm is glued onto this spacer/capillary layer in order to, on the one hand, form an upper border to the capillaries and, on the other hand, to ensure that samples/blood passes from the capillary into the overlying analyte detection zone.

The Scrynell net is arranged on the spacer layer in such a manner that the first 5 mm of the capillaries are not covered by the net and can thus be used as a sample application zone.

The blood-separating membrane coated with the reactive film according to the method described in section 2 and attached at the sides by means of two hot-melt adhesive beads, is located above the Scrynell net (uncoated, blood-separating membrane side facing downwards; reactive film facing upwards).

The configuration of the test strip functional model is comparable with the test strip described in example 1 and FIG. 1 of the EP application No. 04 023 724 (dated May 10, 2004).

4 Assessment of the Functional Model Using Blood Samples Containing Triglycerides 25 μl blood is applied to the sample application zone (capillary area in front of the Scrynell net) on the test strip functional models. The models are measured from above (reactive film side of the membrane) by reflection photometry over a period of 3 minutes at 10 second intervals using an optical measuring system with an LED at the main wavelength of 660 nm.

The measurement procedure is described in the following:

Before applying the sample, the test strip is measured once while excluding ambient light in order to obtain the reflectivity of each unreacted reactive film. The "blank value" of the test strip obtained in this manner is set as 100% relative reflectance (R) for the subsequent kinetic measurement in the presence of sample material.

After applying 25 μl blood the kinetic measurement is immediately started. The reflectivities obtained in the kinetic mode are divided by the respective blank value of the test strip and plotted graphically as relative reflectance (R in %) versus the measuring time.

FIG. 1 shows the kinetic measurement time course obtained in this manner for test strips (containing a "Moist-coated" membrane) in the presence of blood samples having different triglyceride contents (65, 207, 294, 494 and 728 mg/dl).

As the curve time courses of the kinetic measurement show, the color development of the reactive film reaches a reflectance minimum (maximum color depth) within the selected measurement period and this reflectance minimum is selected in the following as a measure of the analyte concentration in the sample.

The relative reflectance minima (in %) are listed in the following table 2 for a "moist-coated" and a "dry-coated" BTS-SP-300 membrane containing an identical reactive film in increasing order for blood samples having different triglyceride contents.

TABLE 2

| triglyceride content in the blood sample | % relative reflectance (in the minimum) | |
|---|---|---|
| | "moist-coated" membrane | "dry-coated" membrane |
| 65 mg/dl | 74.7% | 81.6% |
| 76 mg/dl | 71.7% | 81.5% |
| 100 mg/dl | 69.4% | 81.3% |
| 105 mg/dl | 68.7% | 77.7% |
| 142 mg/dl | 63.5% | 77.3% |
| 154 mg/dl | 63.1% | 77.8% |
| 207 mg/dl | 59.0% | 75.7% |
| 217 mg/dl | 56.9% | 72.6% |
| 265 mg/dl | 52.6% | 72.3% |
| 294 mg/dl | 48.7% | 70.3% |
| 326 mg/dl | 48.8% | 71.5% |
| 384 mg/dl | 47.3% | 68.6% |
| 494 mg/dl | 44.2% | 64.3% |
| 728 mg/dl | 36.1% | 57.5% |
| Total reflectance range | 38.6% | 24.1% |

As shown in table 2 the functional models containing the "moist-coated" membrane generate considerably more color (lower reflectance values) over the entire measuring range than the "dry-coated" membrane containing an identical reactive film.

Figure 2:
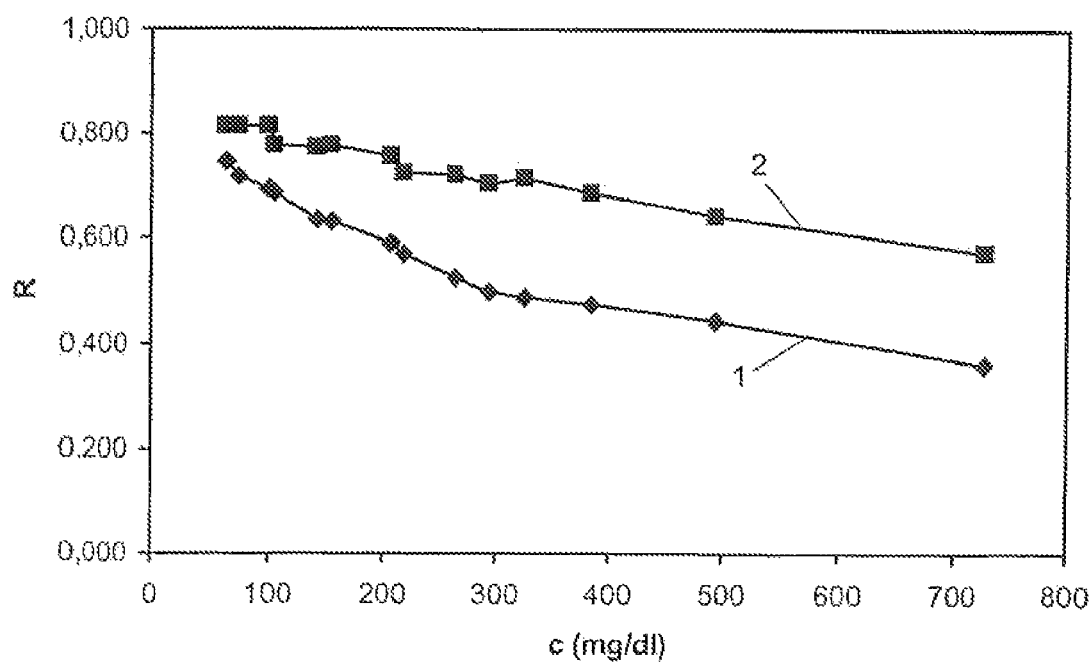
FIG. 2 shows the relative reflectance (R) at different triglyceride concentrations (c in mg/dl) in blood samples for dry-coated (2) and moist-coated (1) membranes.

Furthermore, the measured values show that the reflectance range (i.e., the difference between the relative reflectances for the triglyceride concentrations 65 mg/dl and 728 mg/dl) achieved over the entire measuring range is considerably larger for the "moist-coated" membrane at 38.6% REM than the reflectance range for the "dry-coated" membrane at 24.1% REM (see also the graphic curve shown in FIG. 2, in which 1 is the measurement curve for the moist-coated membrane and 2 is the measurement curve for the dry coated membrane).

Due to the considerably larger reflectance range for the "moist-coated" membrane the variations in reflectance from measurement to measurement result in a considerably lower variation in concentration and thus in a higher precision of the functional model.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although sole aspects of the present invention are identified herein as preferred or particularly advantageous, it is contemplated that the present invention is not necessarily limited to these preferred aspects of the invention.

What is claimed is:

1. A method for applying reactive films containing solids to microporous, absorbent, blood-separating membranes comprising:

providing a microporous membrane, said membrane capable of generating plasma or serum from whole blood;

providing a water-resistant and/or water-insoluble reactive film containing solids, the reactive film further containing film formers and film openers, wherein said film openers are inorganic or organic particulate fillers, the amount of filler being greater than the amount of film former, said reactive film further containing at least portions of a detection reagent for an analyte, said detection reagent being provided in a hydrophobic matrix of film formers;

moistening the microporous membrane with water or an aqueous solution; and applying the reactive film to the microporous membrane while said membrane is still moist, thereby providing an article comprising a microporous membrane layer and a water-resistant and/or water-insoluble reactive film layer, said microporous membrane layer and said reactive film layer being different layers.

2. The method according to claim 1, wherein the reactive film further contains optically blocking pigments, wetting agents, swelling agents, and combinations thereof.

3. The method according to claim 1, wherein the film opener to film former mass ratio is about 10:1 to about 1:1.

4. The method according to claim 3, wherein the film opener to film former mass ratio is about 5:1 to 2:1.

5. The method according to claim 1 further comprising applying the reactive film to the membrane directly after moistening.

6. The method according to claim 1 further comprising moistening the membrane by bath impregnation, spraying or combinations thereof.

7. The method according to claim 6 further comprising moistening the membrane with water or an aqueous solution by application with a slotted nozzle.

8. The method according to claim 1, wherein the water or the aqueous solution contains a surfactant.

9. The method according to claim 1 further comprising applying the reactive film by knife coating, roller application, slot die coating or combinations thereof.

10. A microporous, absorbent, blood-separating membrane formed by the method according to claim 1.

\* \* \* \* \*